(12) United States Patent
Colan

(10) Patent No.: US 10,098,954 B2
(45) Date of Patent: Oct. 16, 2018

(54) COMPOSITIONS USEFUL IN ALLEVIATING PULMONARY CONGESTION AND USES THEREOF

(71) Applicant: Laura Colan, Tucson, AZ (US)

(72) Inventor: Laura Colan, Tucson, AZ (US)

(*) Notice: Subject to any disclaimer, the term of this patent is extended or adjusted under 35 U.S.C. 154(b) by 0 days.

(21) Appl. No.: 15/182,798

(22) Filed: Jun. 15, 2016

(65) Prior Publication Data

US 2016/0367613 A1    Dec. 22, 2016

Related U.S. Application Data

(60) Provisional application No. 62/180,818, filed on Jun. 17, 2015.

(51) Int. Cl.

| | |
|---|---|
| *A61K 47/10* | (2017.01) |
| *A61K 36/889* | (2006.01) |
| *A61K 36/53* | (2006.01) |
| *A61K 9/08* | (2006.01) |
| *A61K 36/80* | (2006.01) |
| *A61K 31/409* | (2006.01) |
| *A61K 33/14* | (2006.01) |
| *A61K 33/18* | (2006.01) |
| *A61K 9/00* | (2006.01) |

(52) U.S. Cl.
CPC ............ *A61K 47/10* (2013.01); *A61K 9/0056* (2013.01); *A61K 9/08* (2013.01); *A61K 31/409* (2013.01); *A61K 33/14* (2013.01); *A61K 33/18* (2013.01); *A61K 36/53* (2013.01); *A61K 36/80* (2013.01); *A61K 36/889* (2013.01); *A61K 9/0043* (2013.01); *A61K 9/0073* (2013.01); *A61K 9/0078* (2013.01)

(58) Field of Classification Search
None
See application file for complete search history.

(56) References Cited

U.S. PATENT DOCUMENTS 6,203,796 B1 *  3/2001  Papaprodromou .... A61K 36/53
                                                        424/400

OTHER PUBLICATIONS

English abstract of Guo (CN 10318565 A—2013).*

* cited by examiner

*Primary Examiner* — Susan Hoffman
(74) *Attorney, Agent, or Firm* — Abelman, Frayne & Schwab

(57) ABSTRACT

The invention relates to a congestion alleviating composition. The composition contains chlorophyll, tincture of pau d'arco, an herbal oil with antiviral properties, such as oil of oregano, coconut oil, and iodized salt as essential components.

16 Claims, No Drawings

COMPOSITIONS USEFUL IN ALLEVIATING PULMONARY CONGESTION AND USES THEREOF

RELATED APPLICATION

This application claims priority to U.S. Provisional Application No. 62/180,818 filed Jun. 17, 2015, incorporated by reference in its entirety.

FIELD OF THE INVENTION

This invention relates to compositions and methods which are useful in addressing pulmonary congestion, and complications which arise from it, as well as pulmonary congestion arising from other conditions. More specifically, it relates to a formulation, preferably but not necessarily in liquid form, which can be used in various ways, such as gargles, nasal rinses, neti pots, vaporizers, nebulizers, and other modes known to the art.

BACKGROUND AND PRIOR ART

It is well known that various conditions, e.g., bacterial, fungal, or viral infections, and contact with environmental stimuli such as pollen and dander cause congestion in the pulmonary systems of affected individuals. Asthmatics, individuals suffering from bronchitis, "thrush" or other yeast or fungal infections, allergy sufferers, etc., all experience the build-up of mucus, phlegm, and other matter which impedes the ability to breathe easily or comfortably. In some cases, the build-up of these materials is such that the condition ceases to be inconvenient or a symptom of another disease, and instead becomes a condition in and of itself, requiring treatment.

It should be noted that build up of the materials set forth supra, is not limited to what would be considered a pathological condition. Many individuals will speak of "feeling congested" as a result of, e.g., weather conditions, smoky rooms, exposure to allergens, and so forth. The resulting discomfort has been described as, having a heavy weight on one's chest, a sense of severe constriction of the rib cage, a feeling of drowning, and so forth.

The standard approach to alleviating these conditions is the administration of an expectorant. Many of these products, sold over the counter or prescribed, contain harsh, harmful ingredients, are only minimally effective, or both. Indeed, when pressed to recommend a good expectorant, many health care providers have no suggestions, in view of the dearth of useful products available.

It is the purpose of the invention described herein to provide a safe, easily usable, biodegradable formulation which facilitates alleviation of congestion. How this is accomplished is shown in the Detailed Description which follows.

DETAILED DESCRIPTION OF PREFERRED EMBODIMENTS

The formulation of the invention is effective for alleviation congestion of the pulmonary system via, e.g., reducing of noxious materials, such as, but not limited to mucus, phlegm, molds, viruses, bacteria, and other microbial agents, environmental components (e.g., pollen and dander) and other built up liquid and semi-solid materials in the lungs or other parts of the mammalian, especially human, respiratory system.

The compositions of the invention contain liquid chlorophyll, pau d'arco tincture, oil of oregano, coconut oil, and iodized sea salt. More particularly, they contain from about 15 to about 50 ml of liquid chlorophyll, from about 15 to about 50 ml of tincture of pau d'arco, from about 0.25 to about 0.75 ml of an antiviral herb oil, preferably oil of oregano, from about 0.25 to about 0.75 ml of coconut oil, and from about 2 to about 3 grams of iodized salt. In an especially preferred embodiment, the composition of the invention embodies:

- about 15 ml liquid chlorophyll;
- about 15 ml pau d'arco tincture;
- about 0.25 to about 0.50 ml oregano oil;
- about 0.25 to about 0.50 ml coconut oil, and
- about 2.5-3.0 grams iodized salt.

More preferably, the liquid chlorophyll is an isotonic $H_2O$ based, glycerin solution, the tincture is alcohol free, and the iodized salt is iodized sea salt.

The formulation of the invention is used by adding it to from 12 to 16 ounces of water, with stirring. The formulation mixes better in warm water, and purified water is preferred.

The resulting solution may be used as a gargle, where the user takes a sufficient amount of the solution into the mouth so that it is half filled, and then gargles, for anywhere from 2 to 20 seconds, after which the solution is expelled, and the consumer continues until the entire solution has been used. Various approaches to using the formulation effectively may be employed. Perhaps most efficaciously one either hums a familiar song, or the standard harmonic scale. One can use more expensive, prescription devices, such as the so-called lung flute (U.S. Pat. No. 6,984,214) or "acapella mucus clearance" device; however, an advantage of the present invention is precisely that no special equipment is necessary.

The above formulations constitute a single dose of the formulation of the invention. When a bulk quantity of the product is desired, one of skill in the art will see that the percentages, by volume, can be from 40-48% liquid chlorophyll, from 40-49% pau d'arco tincture, and from 0.5 to 1% of each of oregano oil, coconut oil, and iodized salt.

The skilled artisan will recognize that "tincture", as used in medicinal, herbal, and chemical arts, can refer to various concentrations of an active substance, as well as diverse carriers. As used, herein "tincture" preferably refers to non-alcoholic tinctures of from 1% to 10%, preferably 2%-7%. Aqueous tinctures are exemplary.

With respect to the herbal oil, any of the herbal oils with antiviral efficacy (e.g., cilantro, sage, and oregano), can be used. Various concentrations are also possible, be they "straight," i.e., 100% herbal oil, or anywhere from 100% to even 5%. Usually, the carrier for these dilutions is olive oil, but any pharmaceutically safe oil can be used as a carrier. The concentration of the oil should be one such that a total of anywhere from 1 mg to 50 mg of herbal oil are present in the formulation; preferably, from 1 mg to 5 mg and most preferably, about 3.25 mg. A major factor in the amount of oil used is the consumer's tolerance for it, as some consumers find the taste of some of the oils unpleasant and will require lower concentrations.

For example, the preferred herbal oil (oil of oregano) has a very strong taste to some users, and they will require a smaller amount than other oils which may be used. Similarly, some users find the taste of cilantro unpleasant and formulations may be modified.

With respect to the liquid chlorophyll, the chlorophyll is present in a pharmaceutically acceptable carrier. Glycerin is preferred, as chlorophyll is not as soluble in water as it is in glycerin. The source of the chlorophyll can vary, but chlorophyll extracted from alfalfa is common. A solution of chlorophyll is preferred which provides from about 20 to about 50, most preferably from 25-35 (e.g., 33⅓) mg of chlorophyll per teaspoon of the chlorophyll solution.

Other embodiments of the invention will be clear to the skilled artisan and need not be reiterated herein.

The terms and expression which have been employed are used as terms of description and not of limitation, and there is no intention in the use of such terms and expression of excluding any equivalents of the features shown and described or portions thereof it being recognized that various modifications are possible within the scope of the invention.

The invention claimed is:

1. A method for alleviating pulmonary congestion, comprising administering an amount of a composition comprising:
   (i) liquid chlorophyll;
   (ii) tincture of pau d'arco;
   (iii) an antiviral herbal oil selected from the group consisting of cilantro oil, sage oil, and oil of oregano;
   (iv) coconut oil; and
   (v) iodized salt
   sufficient to provoke expectoration of mucus or phlegm, to a subject suffering from congestion.

2. The method of claim 1, further comprising a pharmaceutically acceptable carrier.

3. The method of claim 2, wherein said pharmaceutically acceptable carrier is water.

4. The method of claim 1, wherein said tincture of pau d'arco contains from 1% to 10% pau d'arco in an aqueous tincture.

5. The method of claim 4, wherein said tincture of pau d'arco contains 2% to 7% pau d'arco in an aqueous solution.

6. The method of claim 1, wherein said antiviral herbal oil is admixed with a pharmaceutically acceptable oil.

7. The method of claim 6, wherein said pharmaceutically acceptable oil is olive oil.

8. The method of claim 1, wherein said liquid chlorophyll is in a glycerin solution.

9. The method of claim 1, wherein said iodized salt is sea salt.

10. The method of claim 1, wherein said antiviral herbal oil is oil of oregano.

11. The method of claim 10, wherein said composition comprises:
    (i) from about 15 ml to about 50 ml liquid chlorophyll;
    (ii) from about 15 ml to about 50 ml of tincture of pau d'arco;
    (iii) from about 0.25 ml to about 0.75 ml of oil of oregano;
    (iv) from about 0.25 ml to about 0.75 ml coconut oil, and
    (v) from about 2 to about 3 grams iodized salt.

12. The method of claim 11, wherein said composition comprises:
    (i) about 5 ml liquid chlorophyll;
    (ii) about 15 ml tincture of pau d'arco;
    (iii) about 0.25 to about 0.50 ml oil of oregano;
    (iv) from about 0.25 to about 0.50 ml of coconut oil, and
    (v) from about 2.5 to about 3 grams iodized salt.

13. The method of claim 11, wherein said composition consisting of:
    15 ml liquid chlorophyll;
    15 ml pau d'arco tincture;
    from 0.25 to 0.50 ml oregano oil;
    from 0.25 to 0.50 ml coconut oil; and
    from 2.5 to 3 grams iodized salt.

14. The method of claim 1, comprising administering said composition in a form of a gargle.

15. The method of claim 14, comprising gargling for from 2 to 20 seconds.

16. The method of claim 15, comprising repeating said gargling until a total of from 12 to 16 ounces of said composition have been used.

* * * * *